United States Patent [19]

Miller, Jr. et al.

[11] Patent Number: 5,252,495
[45] Date of Patent: Oct. 12, 1993

[54] IMMUNOASSAY FOR PHYSOSTIGMINE

[75] Inventors: Russell L. Miller, Jr., Washington, D.C.; Pritam S. Verma, Adelphi, Md.

[73] Assignee: Howard University, Washington, D.C.

[21] Appl. No.: 853,850

[22] Filed: Mar. 19, 1992

Related U.S. Application Data

[63] Continuation of Ser. No. 372,691, Jun. 26, 1989, abandoned.

[51] Int. Cl.$^5$ ............... G01N 33/531; G01N 33/534; G01N 33/53; A61K 35/14
[52] U.S. Cl. .................................. 436/542; 436/543; 436/545; 436/547; 436/804; 424/88; 530/389.8; 435/7.1
[58] Field of Search ................ 436/542, 543, 536; 486/544; 530/350, 403

[56] References Cited

U.S. PATENT DOCUMENTS

| | | | |
|---|---|---|---|
| 2,909,530 | 10/1959 | Rudner | 548/429 |
| 4,078,049 | 3/1978 | Felix et al. | 424/1 |
| 4,278,667 | 7/1981 | Madison et al. | 424/232 |
| 4,278,679 | 7/1981 | Madison et al. | 424/263 |
| 4,591,573 | 5/1986 | Verma | 436/542 |

OTHER PUBLICATIONS

Groff et al. J. Pharm. Sci. 66(3):389 (1977).
Gennings et al. Fund. & Appl Toxicol. 14:235 (1990).
Leadbeater et al. Fun Applied Toxicol 5:S225 (1985).
Somani et al. Int. J Clin Pharm, Ther. Toxi. 25(8)412 (1987).
Lukey et al. J. Chromat. 493:117 (1989).
Groff et al. U.S. NTIS. AD Rep. AD-A023121 17 pages from Gov. Rep. Annouc. Index (U.S.) 76(12)68 (1976).
Meyer et al. J. Pharm. Exp. Therap. 251(2):606 (1989).
Miller et al. J. Pharm. & Biom. Anal 7(8):955 (1989).
Latha et al. Life Sciences. 36:1389-96 (1985).
Hurst et al. Biomed Chromat. 3(5):226 (1989).
Erlanger B. (1973) Principles & Methods for the Preparation of Drug protein Conjugates Pharmacol. Reviews. 25(2) 271-80.
Lukey et al. (1988) Radiometric high-performance Liquid Chromatography assay for Physostigmine Chem. Abs. 111(17)148164n.

*Primary Examiner*—Robert A. Wax
*Assistant Examiner*—Miguel Escallon
*Attorney, Agent, or Firm*—Kenyon & Kenyon

[57] ABSTRACT

A radioimmunoassay for physostigmine in biological fluids. The method disclosed can detect 100 pg of physostigmine per ml of biological fluid using 0.1 ml of biological fluid. The antibody used in this method can be raised from an antigen produced by either or two methods—diazotizing para-aminobenzoic acid and reacting the diazotized material with physostigmine to form a physostigmine-hapten solution, which is then reacted with bovine serum albumin or by using a Mannich reaction to directly conjugate physostigmine to bovine serum albumin. The antibody used in the disclosed method has a cross-reactivity with the major metabolites of physostigmine of less than 1%.

8 Claims, 4 Drawing Sheets

IMMUNOASSAY FOR PHYSOSTIGMINE

This application is a continuation of application Ser. No. 07/372,691, filed Jun. 26, 1989, now abandoned.

FIELD OF INVENTION

The invention relates to a immunoassay for physostigmine in biological fluids. More particularly, the invention relates to a sensitive and specific radioimmunoassay for physostigmine which involves producing antibodies from a physostigmine containing hapten-bovine albumin complex. The radioimmunoassay of this invention detects physostigmine quantities as low as 100 pg of physostigmine per 0.1 ml of biological fluid.

BACKGROUND OF THE INVENTION

Physostigmine is a tertiary amine which can be isolated from the seed of the physostigma venenosum balfour, a plant native to coastal areas of Africa. Physostigmine is soluble in biological fluids and salts of physostigmine, e.g., sulfate and salicylate, have many therapeutic uses. These salts are usually colorless, odorless crystals which gradually turn red upon exposure to air and light. The rate of color change is enhanced in the presence of moisture. Physostigmine salts are soluble in water, but are unstable in alkaline solutions.

Physostigmine is a reversible cholinesterase inhibitor which prevents the hydrolysis of acetylcholine by competing with acetylcholine for attachment to acetylcholinesterase. Acetylcholine is a neurotransmitter stored in vesicles where it is primarily released by nerve impulses. The vesicles migrate towards the terminal synaptic membrane during nerve stimulation and disgorge acetylcholine by exocytosis. Upon release from the cholinergic nerve endings, acetylcholine is inactivated by enzymatic degradation. The inactivation is accomplished by the hydrolysis of acetylcholine by cholinesterase. The specific cholinesterase for acetylcholine, acetylcholinesterase, is quite efficient—one molecule of the enzyme is able to hydrolyze $3 \times 10^5$ molecules of acetylcholine per minute.

Because a physostigmine-acetylcholinesterase enzyme complex hydrolyzes at a much slower rate than the corresponding acetylcholine-acetylcholinesterase enzyme complex, acetylcholine accumulates at the cholinergic synapses. Due to the reversible nature, i.e., uncoupling, of the physostigmine-acetylcholinesterase complex, physostigmine appears to facilitate the transmission of impulses across the myoneural junction.

There are several clinical uses for reversible cholinesterase inhibiting agents such as physostigmine. Physostigmine is used to improve muscle strength in the symptomatic treatment of mysthenia gravis. Parental physostigmine is also useful in reversing of the effects of nondepolarizing neuromuscular blocking agents, e.g., tubocurarine, metocurine, gallamine or pancuronium, after surgery. Recently, cholinesterase inhibitors have been used in an attempt to reverse certain degenerative disorders of the central nervous system. Moreover, physostigmine may be of value in the treatment of cognitive disorders which involve disturbances of memory. For example, it has been suggested that since cognitive changes observed during the aging process, e.g., Alzheimer's syndrome, may be related to gradual reductions in acetylcholine in various parts of the brain, the administration of physostigmine might help reduce or reverse the observed cognitive changes.

Physostigmine may also be used to block intoxication by irreversible cholinesterase inhibitors. Reversible cholinesterase inhibitors, such as physostigmine, have been proposed as antidotes to nerve agents used in chemical warfare. Many nerve agents are organo-phosphorous compounds which are readily vaporized under normal atmospheric conditions. The extreme toxicity of such organo-phosphorous compounds are related to their short-lived, but irreversible, destruction of the functioning of nerves and organs. By phosphorylating acetylcholinesterase, these organo-phosphorous compounds form stable, irreversible complexes with acetylcholinesterase. The formation of such stable complexes permanently prevents the normal function of acetylcholinesterase, i.e., the termination of acetylcholine actions at synaptic, particularly neuromuscular, junctions. Since the enzyme is completely and permanently prevented from binding with acetylcholine, the acetylcholine quickly accumulates at receptor sites to a degree sufficient to produce loss of function in target nerves and organs.

From animal studies, it has been proposed that nerve agent toxicity can be prevented by the preadministration of a short acting, reversible cholinesterase inhibitor such as physostigmine. The physostigmine would temporarily bind acetylcholinesterase in the tissue which would prevent its phosphorylation by the nerve agents and the resulting irreversible inactivation of the active site of the acetylcholinesterase.

To date, however, results obtained from the administration of cholinesterase inhibitors such as physostigmine to maintain, restore or increase acetylcholine levels in patients, including those with Alzheimer's syndrome, have been equivocal. A primary problem encountered with the clinical use of physostigmine has been that it is toxic at levels very close to those which produce therapeutic results. For example, in certain patients physostigmine has been associated with adverse effects typical of exaggerated responses to parasympathetic stimulation including adverse muscarinic effects such as nausea, vomiting, diarrhea, miosis, excessive salivation and sweating, abdominal cramps, bradycardia, bronchial secretion and bronchospasm. Other side effects of physostigmine include generalized weakness, muscle cramps, fasciculation, hypotension, and, if administered intraveneously, thrombophlebitis. A substantial over administration of physostigmine causes cholinergic crisis leading to death.

Although physostigmine is widely used in clinical medicine, there is no simple and reliable method to measure minute concentrations of the drug in biological fluids. Moreover, relatively little is known about the pharamacokinetic parameters, i.e., the change in concentration at various sites, including absorption, distribution, metabolism and excretion, of physostigmine in man. The dearth of information is due primarily to the lack of a satisfactory analytical method for repeatedly measuring low concentrations of physostigmine in biological fluids.

Presently, a quantitative assay using human blood is available to measure the amount of physostigmine. This assay is based on the duration of cholinesterase inhibition and can detect microgram quantities of physostigmine. A high pressure liquid chromatography (HPLC) method is available which can detect 50 ng of physostigmine in a biological sample. These methods, however, are not sufficiently sensitive for the study of the drug's kinetics using plasma and tissue samples. Tritiated physostigmine has been used to study the pharmacokinetics of the drug in laboratory animals. This method is sensitive but would not be suitable to monitor plasma concentrations of the drug in clinical situations. In fact, all of the presently known methods are insufficient or too expensive and suggest the need for a sensitive, specific, cost effective method for the monitoring of physostigmine concentrations in biological samples.

There are several reasons why such analytical methods for measuring physostigmine in biological fluids have been unsatisfactory. The amounts of physostigmine to be measured are extremely low, which means that any analytical method must be sufficiently sensitive to detect extremely low levels of physostigmine. Moreover, physostigmine undergoes extensive in vitro hydrolysis in biological solutions, particularly in plasma and blood and the method must be specific so that metabolites are not measured as physostigmine.

While radioimmunoassay (RIA) procedures are widely used in clinical and research laboratories to determine the minute quantities of numerous substances in biological fluids, heretobefore an immunoassay for determining the presence of physostigmine in such fluids has been unavailable, primarily because the physostigmine molecule is very small and can not stimulate the immune systems of animals to produce antibodies. The inability to stimulate the immune system is further complicated by the fact that the physostigmine molecule contains few of the functional groups which are usually necessary for a molecule to be linked to a protein immunogen.

Moreover, because of its small size, it was believed that an immunogen for physostigmine might lack sufficient selectivity to avoid cross reactivity with the metabolites of physostigmine and other reversible cholinesterese inhibitors or the metabolites thereof. Since the degradation products are 1000 times less potent than the physostigmine in the inhibition of cholinesterase, it is important to specifically measure the parent compound. The binding of small amounts of metabolites to the antibody could result in significant errors in the measurement of the amount of physostigmine induced anticholinesterase activity present.

It is therefore an object of the present invention to provide for a method for the determination of the amount of physostigmine in biological fluid.

It is another object of the present invention to provide an immunoassay for the determination of the amount of physostigmine in biological fluids.

Yet another object of the present invention is to provide immunogens which after injection into animals will result in the production of antibodies for use in an immunoassay for the determination of physostigmine in biological fluids.

Still a further object of the present invention is to provide monoclonal and polyclonal/antibodies which can be used to determine physostigmine in biological fluids.

A further object of the present invention is to provide for a method of measuring physostigmine in biological fluids which facilitates the study of the pharmacokinetics of physostigmine.

Still another object of the present invention is to provide for a reduction in the toxicity and other adverse side effects which results from the clinical use of physostigmine.

These and other objects of the present invention, as will become more readily apparent hereinafter, are achieved by the invention described herein below.

SUMMARY OF THE INVENTION

The invention provides a sensitive and specific radioimmunoassay (RIA) for physostigmine which detects quantities as low as 100 pg of physostigmine per ml of biological fluid, using a 0.1 ml sample of biological fluid, without extraction. The invention provides for immunogens in which physostigmine has been conjugated to bovine serum albumin (BSA) by different methods. In one method, the immunogen is made by first diazotizing PABA (p-aminobenzoic acid) and then reacting it with physostigmine to form a physostigmine-PABA hapten. The hapten is then reacted with the BSA. In the second method, the Mannich reaction is used to directly conjugate physostigmine to BSA. The immunogen, as synthesized by either method, is then administered to an animal and the resultant serum containing antibodies is harvested from the animal's blood. The harvested serum then is used in the RIA at a final dilution of 1:150, if derived from the physostigmine-PABA hapten, or 1:100, if derived from the Mannich conjugation.

Using the RIA of the present invention, the pharmacokinetics of physostigmine can be studied. The RIA of the present invention is extremely sensitive and accurate. For example, while detecting quantities as low as 100 pg of physostigmine per 0.1 ml of biological fluid, the major metabolites of physostigmine do not cross-react with the antibodies raised in response to the physostigmine immunogen. The specificity of the RIA has been validated by using the high pressure liquid chromatography (HPLC) method for physostigmine detection.

DETAILED DESCRIPTION OF THE INVENTION

Figure 1:
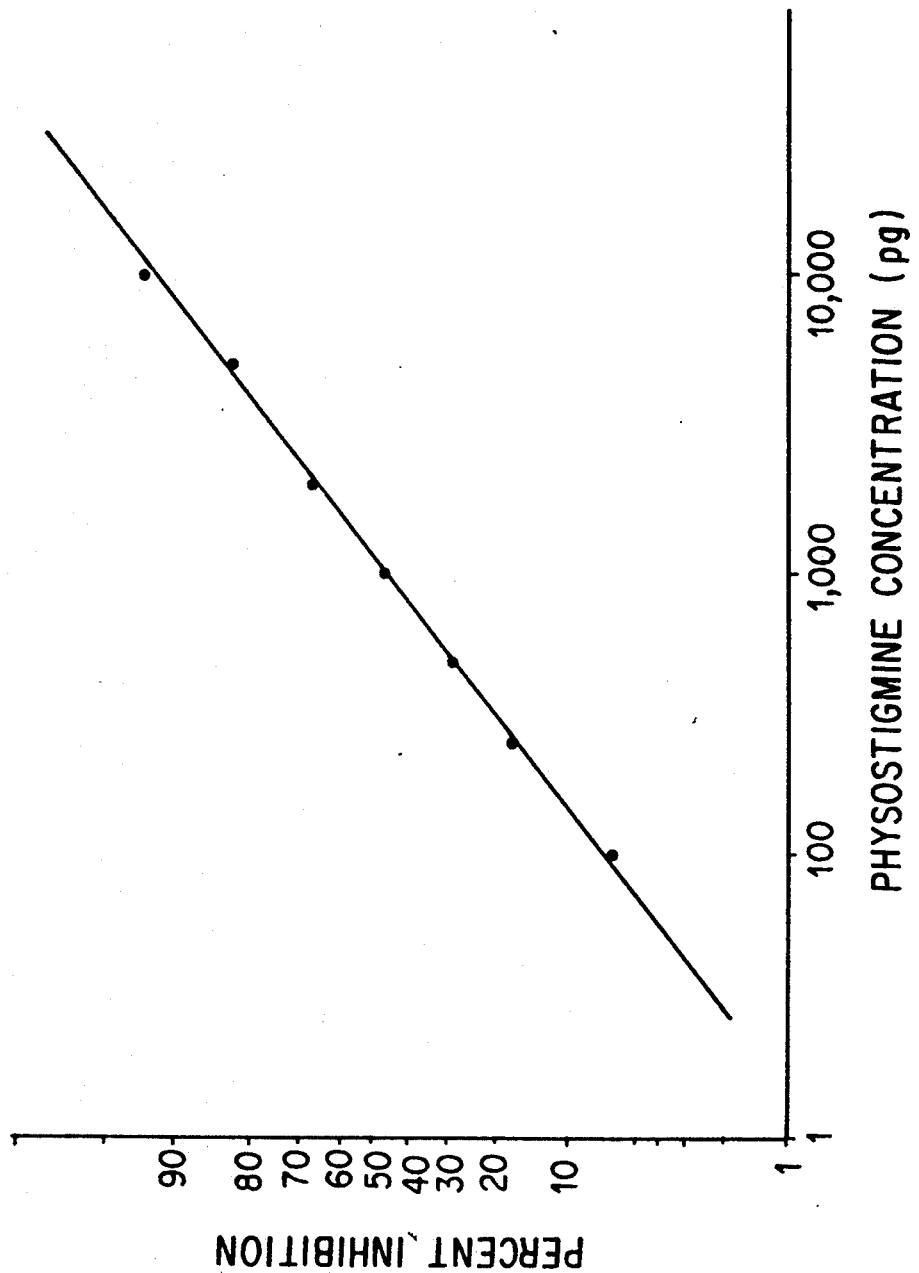
FIG. 1 is the standard linear dose-response (logitlog) curve obtained for both polyclonal antibodies of the present invention.
Figure 2A:
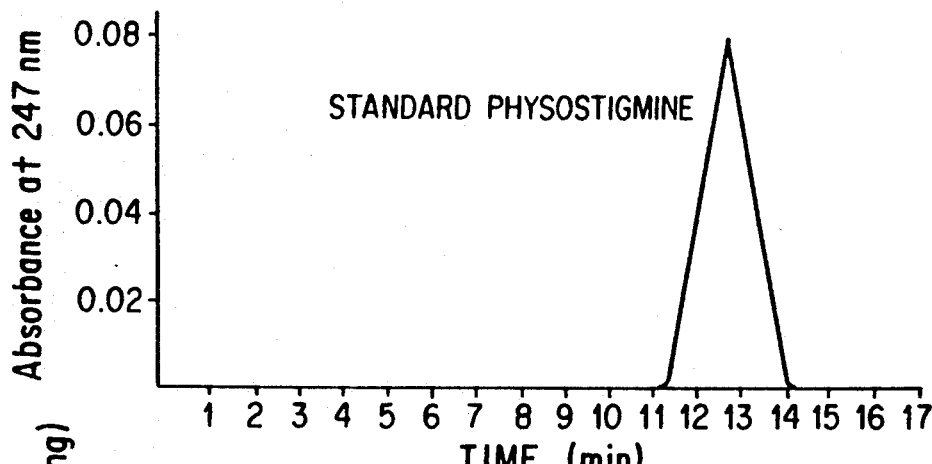
FIGS. 2(A-E) is a series of high pressure liquid chromatographs which confirm the specificity of the RIA of the present invention.
Figure 2B:
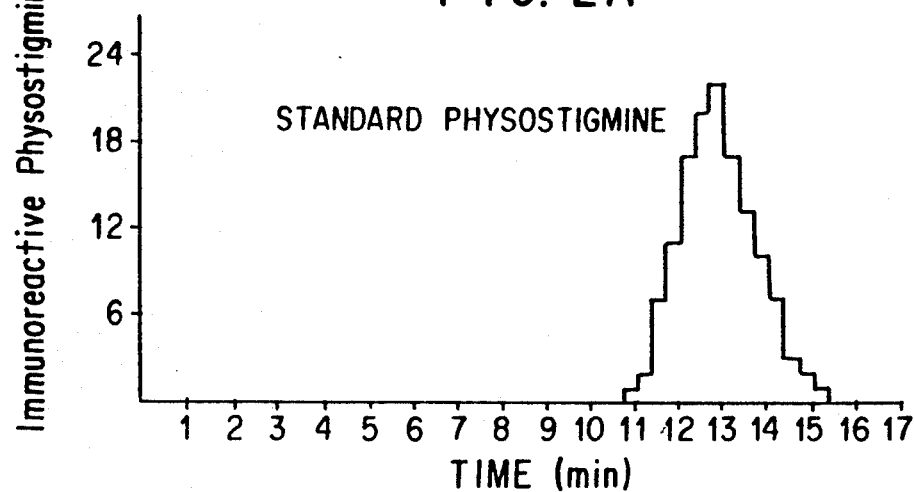
Figure 2C:
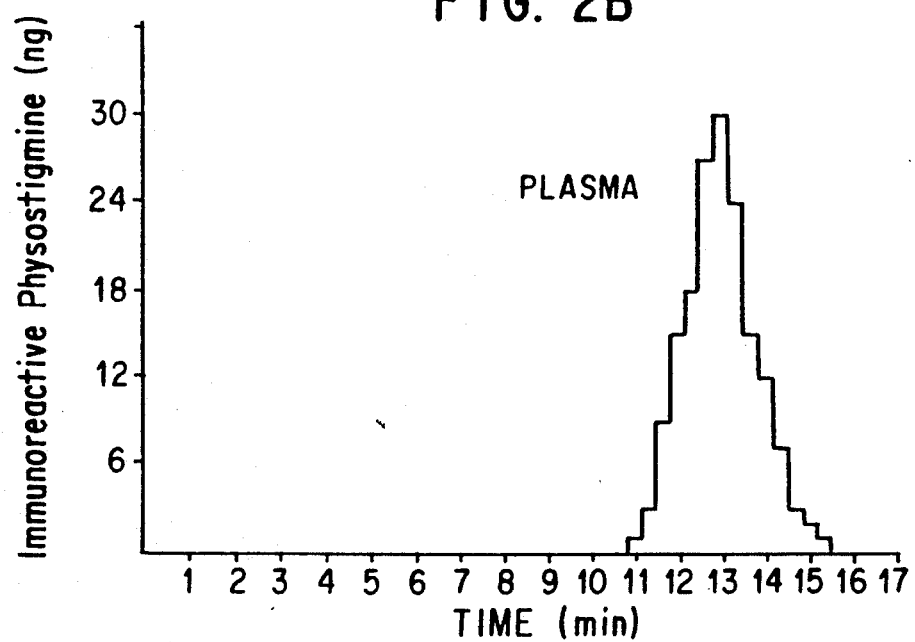
Figure 2D:
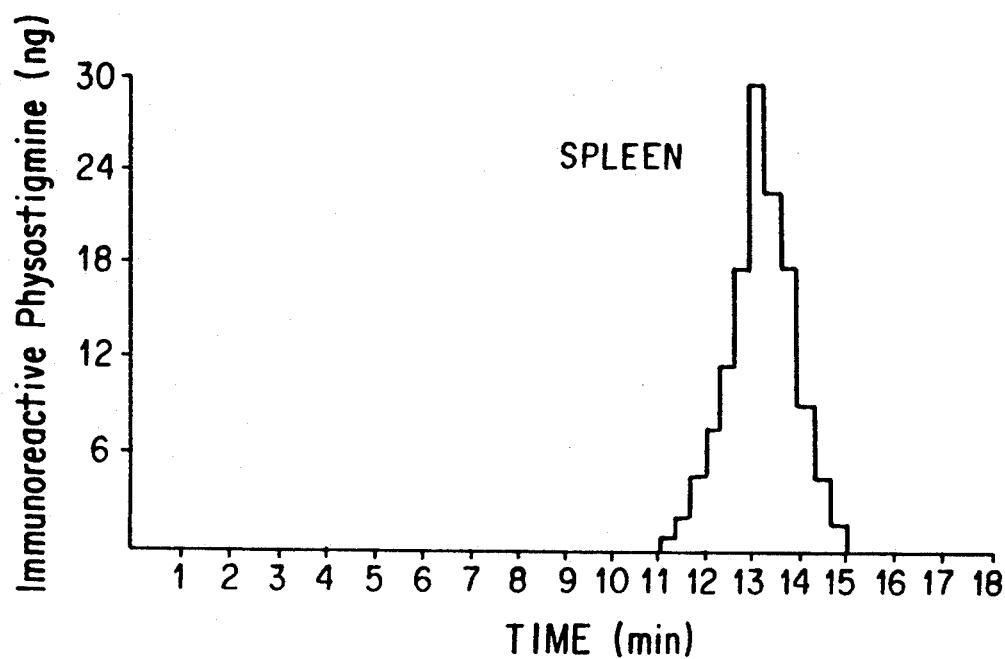
Figure 2E:
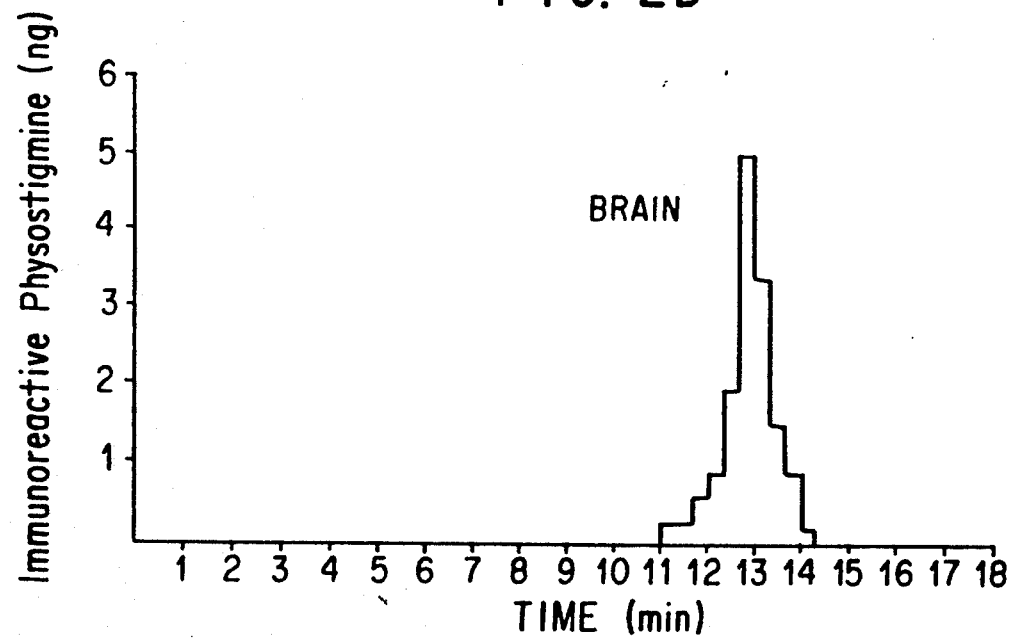

Radioimmunoassay (RIA) is a sensitive procedure for quantitative in vitro measurement of drug levels in biological fluids. RIA is based upon the observation that unlabeled antigen and radioactive-labeled antigen compete to bind with antibody to the antigen in vitro. The essence of the physostigmine RIA, as embodied in the present invention, is that unlabeled physostigmine and radioactively labeled physostigmine compete to bind with antibodies to a physostigmine immunogen in an in vitro reaction mixture. All reaction mixtures, whether for standard curve construction or serum samples, contain set amounts of radioactively labeled physostigmine and antibodies to physostigmine, and a variable amount of physostigmine (standards or serum samples). The antibodies to physostigmine bind either with physostigmine or radioactively labeled physostigmine, with the binding to radioactively labelled physostigmine being dependent upon the amount of unlabeled physostigmine present. As the amount of physostigmine in the reaction mixture increases, the amount of radioactively labeled physostigmine that binds to the available physostigmine antibody decreases.

To assay the concentration of physostigmine in biological fluids, reaction mixtures are set up containing radioactively labeled physostigmine, antibody to physostigmine and a sample of biological fluid. The amount of radioactively labeled physostigmine bound to the physostigmine antibody is measured in counts per minute using a scintillation counter. The amount of physostigmine present then is determined from a standard curve. The standard curve is constructed by experimentally determining that when "X" amount of unlabeled physostigmine standard is introduced into the reaction, "A" amount of labeled physostigmine is recovered bound to physostigmine antibody; and when "Y" amount of unlabeled physostigmine is introduced into the reaction, "B" amount of labeled physostigmine recovered bound to physostigmine antibody, etc. From this data, the standard curve is constructed showing amounts of labeled physostigmine recovered bound to antibody versus unlabeled physostigmine present. Subsequently, when a sample of biological fluid with an unknown amount of physostigmine is assayed in the reaction mixture, and "A" amount of labeled physostigmine is recovered bound to physostigmine antibody, it is determined from the standard curve that "X" amount of physostigmine is present in the biological fluid sample.

The detailed description of the present invention can be more fully understood by the following detailed procedure for a specific embodiment of the invention. While the specific embodiment describes the invention in terms of polyclonal antibodies, it will be apparent to one skilled in the art that the present invention contemplates raising and utilizing monoclonal antibodies in the RIA disclosed therein.

DESCRIPTION OF A PREFERRED EMBODIMENT

As a first step in the RIA, a physostigmine immunogen was prepared. Physostigmine was conjugated to bovine serum albumin (BSA) by two different procedures. In the first procedure diazotized p-aminobenzoic acid (PABA) was reacted with physostigmine under acidic conditions and the product coupled to BSA with carbodiimide. In the second procedure the Mannich reaction was used to conjugate physostigmine to BSA. The detailed procedures for the preparation of the immunogens are given below.

Method 1

0.2 mmole of PABA was dissolved in 2 ml of 1N HCl and the solution was cooled to 4° C. in an ice bath. A solution of 0.18 mmole sodium nitrite in 2 ml ice cold distilled water was added dropwise to the PABA solution with constant stirring and while maintaining the solutions at 4° C. The mixture was stirred gently and the reaction was allowed to proceed for 45 minutes at 4° C. Physostigmine base 0.2 mmole was dissolved in 3 ml 0.1N HCl and 3 ml of a 50% solution of N, N-dimethylformamide; 1.0 uCi of tritiated physostigmine was added. The pH was adjusted to 5.0 and the mixture was cooled to 4° C. The PABA diazonium salt was added dropwise to the physostigmine mixture with constant stirring in an ice bath while maintaining the pH between 5.0 and 6.0. The reaction mixture was covered to protect the reactants from light and left stirring in the cold room for 4 hr.

50 mg Bovine serum albumin (BSA) in 0.1 mmole sodium phosphate buffer was added to the physostigmine hapten solution (pH was adjusted to 6.0). In the presence of 0.5 mmole soluble 1-ethyl-3-(3-dimethylaminopropyl)-carbodiimide. The reaction was allowed to proceed overnight at room temperature. The solution was dialyzed for 48 hours against 100 volumes of distilled water changing the solution every 8 hours, then against 0.9 percent sodium chloride for 16 hours changing the solution every 4 hours. Radioactive measurements of tritiated physostigmine demonstrated that twelve (12) molecules of the physostigmine hapten were conjugated to each BSA molecule.

Method 2

100 mg of BSA was dissolved in 2 ml of distilled water; 1 ml of 3M sodium acetate and 3 ml of 8% formaldehyde solution was added. 0.4 mmole of physostigmine base dissolved in 2 ml of 0.3N HCl and 1.0 uCi of tritiated physostigmine were added to the BSA solution with constant stirring. The pH of the mixture was adjusted to 5.0 and the reaction was allowed to proceed at room temperature for 18 hr. The mixture was dialyzed against distilled water in a cold room (4° C.) for 40 hr. with a change of water every 8 hr. Measurement of radioactivity in the BSA indicated that 6 molecules of physostigmine were conjugated to each molecule of BSA.

Antibodies to the physostigmine-BSA immunogen were produced by injecting male New Zealand white rabbits with immunogens formed by either method. Prior to injection, the immunogen was emulsified with an equal volume of complete Freund's adjuvant, purchased from Difco Laboratories of Detroit, Mich. The initial immunization consisted of 0.8 mg of protein injected intracutaneously in multiple dorsal sites of the rabbits. Booster injections containing 0.8 mg of immunogen and incomplete Freund's adjuvant were administered every two months for the next six months. Antisera was collected one week after each booster injection from the central ear vein. The blood was allowed to clot at room temperature and then centrifuged at 1500×g for 15 minutes. The separated serum was stored frozen at −20° C. until assayed for the presence of physostigmine antibody.

Both immunogens elicited antibody production in each of the animals injected. The presence of antibodies was demonstrated by the binding of tritiated physostigmine to the rabbit serum after the first booster injection. Although the rabbits received several booster injections using each of the immunogens, the titer of antibodies did not change appreciably after the second booster injection. The rabbits injected with the Mannich immunogen produced antibodies which has maximum binding in the RIA at a titer of 1:100 dilution. The rabbits injected with the diazo immunogen produced antibodies which were used in the RIA at a titer of 1:150. The difference in titers of the antibodies may be related to the greater number of physostigmine molecules—twelve versus six—which were attached to diazo immunogen.

In the assay procedure $^3$H-Physostigmine having specificity of 19.0 Ci/mmole and purchased from the Amersham Corp. of Arlington Heights, Ill., was used as tracer. The dilution of tracer (5000 dpm), antibody (1:150) and physostigmine standards (100–10,000 pg) were made using 0.01M phosphate buffer containing 150 mM sodium chloride with a pH of 7.4. The specificity of the antisera is such that in the assay procedure it is used at a final dilution of 1:150 for diazoimmunogen or 1:100 for Mannich immunogen. Both standard and sample tubes were always analyzed in duplicate. The assay was carried out according to the protocol shown in Table 1 with the reagents were added to the assay tubes in the order shown.

TABLE 1

Protocol for the Radioimmunoassay Procedure

| Reagent | Standard Curve Tube | Zero Binding Tube | Nonspecific Binding Tube | Sample Tube |
|---|---|---|---|---|
| | Volume of Reagent Added (ul) | | | |
| PBS (buffer) | 150 | 250 | 350 | 250 |
| Standards | 100 | — | — | — |
| $^3$H-Physostigmine | 50 | 50 | 50 | 50 |
| Diluted antiserum | 100 | 100 | — | 100 |
| Sample | — | — | — | 100 |
| Normal Plasma | 100 | 100 | 100 | — |
| | Vortex and Incubate 3 hr at 4° C. | | | |
| 100% Saturated Ammonium Sulfate | 500 | 500 | 500 | 500 |
| | Centrifuge and Aspirate | | | |
| 50% Saturated Ammonium Sulfate | 1000 | 1000 | 1000 | 1000 |
| | Centrifuge and Aspirate | | | |
| Distilled Water | 1000 | 1000 | 1000 | 1000 |

According to the protocol for the RIA of the present invention, after the addition of antisera, the contents of the tubes were mixed and incubated for 3 hours at 4° C. The antigen which bound to the antibody was separated by adding saturated ammonium sulfate and centrifuging at 2500×g for 15 minutes. After aspiration of the supernatant, the precipitate was washed one time with 50% saturated ammonium sulfate; then the mixture was centrifuged and the supernatent removed. The precipitate was dissolved in 1.0 ml of distilled water, and the solution was transferred to a scintillation vial containing 10.0 ml of acquasol 2.

The radioactivity which was bound to the antibody was determined in counts per minute with a Beckman LS-3133P Liquid Scintillation Counter. FIG. 1 shows the standard dose response curve of the RIA for physostigmine when plotted on a logit-log scale. The concentration of physostigmine is plotted on the horizontal axis, while the percent inhibition of binding radioactively labeled is plotted on the vertical axis. About 100 pg per ml of physostigmine can be distinguished from zero pg. The useful range of the standard curve extends up to 10 ng per assay tube. The addition of 100 ul of normal human or rat serum or plasma had no effect on either the nonspecific binding or the standard curve. Concentrations of physostigmine in unknown samples were determined according to conventional calculations from the standard curve.

The accuracy Of the RIA was determined by adding 200–4000 pg of physostigmine to a measured volume of pooled normal rat plasma. Aliquots were taken and assayed as unknown samples; each concentration was assayed in quadruplicate. The percentage of measured to added physostigmine ranged from 101% to 106%. The inter-assay and intra-assay coefficient of variation were always less than 13%. The non-specific binding was always less than 2% of maximum binding on the standard curve. Neither the addition of plasma nor the supernatant from tissue homogenates had any effect on the standard curve. A three hour incubation period for the RIA was found to be convenience because the percent of binding did not change appreciably between 3 and 8 hr.

To show the stability of physostigmine in biological fluids, physostigmine was added to 2 portions of rat plasma. One half of the plasma was kept at room temperature and the other was kept at 4° C. Aliquots which originally contained 3.6 ng of physostigmine were assayed at various times. Table 2 demonstrates that more than 95% of physostigmine can be recovered from plasma samples that are either processed within 15 min. at room temperature or kept at 4° C. for 3 hr. Since the samples were cooled and processed at 4° C., corrections for loss of physostigmine were unnecessary.

TABLE 2

STABILITY OF PHYSOSTIGMINE IN RAT PLASMA

| | Amount Recovered | |
|---|---|---|
| Time | 23° C. | 4° C. |
| 0 min | 3.6 | 3.6 |
| 15 min | 3.3 | 3.4 |
| 30 min | 3.1 | 3.6 |
| 1 hr | 2.7 | 3.8 |
| 2 hr | 2.8 | 3.6 |
| 3 hr | 2.8 | 3.6 |
| 4 hr | 2.8 | 3.6 |

The antibodies of the present invention are highly specific. The results of RIA determination of the cross-reactivity of the metabolites of physostigmine, related compounds and degradation products are presented in Table 3. Competition of the compounds with labeled physostigmine (5000 dpm) for antibody binding sites was determined arbitrarily at 50% inhibition of the physostigmine on the standard curve. Each compound was tested for cross-reactivity with the antibody. The maximum concentration of each compound tested was 1000 ng.

TABLE 3

Cross-Reactivity of Metabolites and Related Compounds In the Physostigmine Radioimmunoassay

| Compound | Antibody from Diazo-coupled Immunogen IC$_{50}$(ng) | Antibody from Mannich Immunogen IC$_{50}$(ng) |
|---|---|---|
| Physostigmine | 1.35 | 1.35 |
| Eseroline | 200 | 200 |
| Rubreserine | 224 | 248 |
| Eserine brown | 550 | 625 |
| Eserine blue | 600 | 575 |
| Pyridostigmine | >1000 | >1000 |
| Neostigmine | >1000 | >1000 |
| Atropine | >1000 | >1000 |

TABLE 3-continued

Cross-Reactivity of Metabolites and Related Compounds In the Physostigmine Radioimmunoassay

| Compound | Antibody from Diazo-coupled Immunogen IC$_{50}$(ng) | Antibody from Mannich Immunogen IC$_{50}$(ng) |
|---|---|---|
| Acetylcholine | >1000 | >1000 |
| Melatonin | >1000 | >1000 |
| Serotonin | >1000 | >1000 |
| Indomethacin | >1000 | >1000 |
| Paralidoxime | >1000 | >1000 |

As shown in Table 3, 1.35 ng of physostigmine produced a 50% inhibition of the binding of $^3$H-physostigmine to the antibody produced from either immunogen while the up to 100 ng of the major metabolite and 1000 ng of related compounds did not significantly inhibit the binding of labeled physostigmine to the antibody.

The study of the cross reactivity showed that the carbamate group is one of the binding groups necessary for both antibodies to bind to physostigmine. When the carbamate group was removed from physostigmine to form eseroline, almost 150 times as much eseroline was required to displace radioactive physostigmine from the antibodies. The carbamate moeity however, is not the only chemical site on the physostigmine molecule which is required for binding to the antibodies because other anticholinesterase inhibitors which contain the carbamate moeity such as neostigmine and pyridostigmine did not bind to the antibodies.

To study the pharmakinetics of physostigmine and validate the RIA and the antibody specificity of the present invention, rat studies were conducted. Male Sprague-Dawley rats weighing approximately 500 grams were housed two per cage at 23° C. with a twelve hour on-off light cycle. The animals were given food and water ad libitum. After sixty days, food was withheld for twelve hours. Physostigmine, comprised of a physostigmine base dissolved in a small volume of dilute hydrochloric acid and then diluted with phosphate buffered saline, with the pH of the solution adjusted to 6.0 was administered (0.3 mg. of the physostigmine solution/Kg) intramuscularly to the rats. Groups of three animals were sacrificed by using inhalation anesthetic, Fluothane (0.01% thymol, w/w; and 0.00025% ammonia, w/w) Ayerst Laboratories, New York, N.Y. at various times after injection namely at 1, 2, 5, 10, 20, 30, 45, 60, 120, 150 and 180 minutes. Blood, collected via heart puncture, and tissue samples were taken. Brain, fat, heart, muscle and spleen were removed and frozen on dry ice immediately. On the date of analysis the plasma and tissue samples were thawed. The tissues were weighed and homogenized with an equal volume of cold solution of 10 mM EDTA, 150 mM NaCl and 0.5% triton X-100, pH 7.4. The suspension Was centrifuged at 15,000×g in a Sorvall RC-5B centrifuge (Dupont) for 30 min at 4° C. The supernatent was collected and the pellet was Washed and centrifuged. The supernatants were combined and filtered through 1 um pore size filters (RC 60, 9 mm diameter from Schleicher and Schuell Inc., Keene, N.H.) and 100 ul of the filtrate was injected into the HPLC column.

Figure 3:
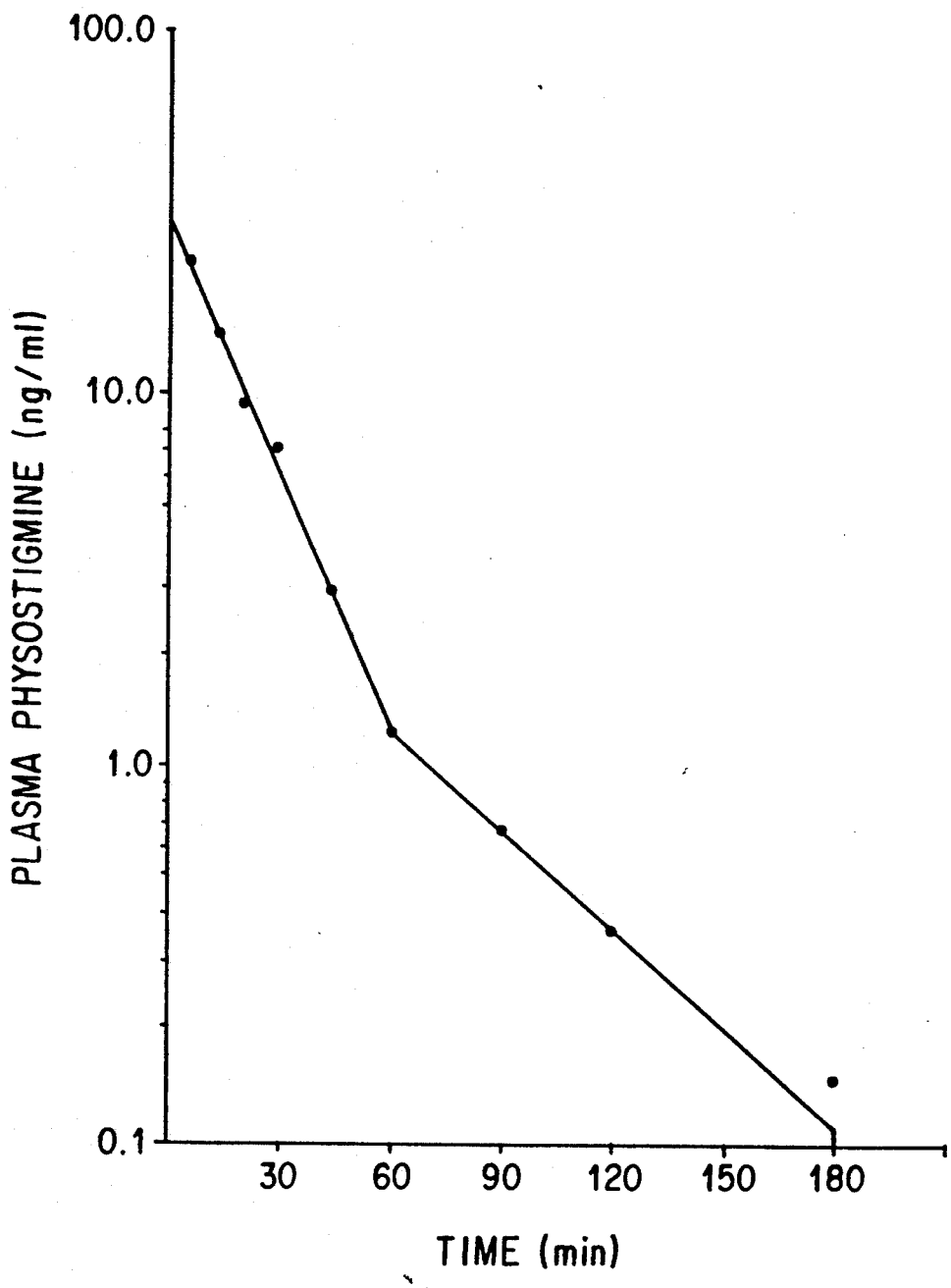
FIG. 3 is the plasma concentration of physostigmine after the intramuscular administration of 0.3 mg/kg physostigmine.

The blood and tissue samples were used to determine the concentration of physostigmine as a function of time. FIG. 3 gives the physostigmine level in the plasma of three male rats for each time interval as determined by the RIA of the present invention, while Table 4 presents the concentration of physostigmine in various organs as a function of time.

TABLE 4

Tissue Concentrations of Physostigmine (ng/g of weight tissue)

| Time Interval (min) | Brain | Fat | Heart | Muscle | Spleen |
|---|---|---|---|---|---|
| 2.5 | 330.51 | 230.00 | 332.14 | 320.55 | 321.84 |
| 5 | 296.61 | 533.33 | 785.05 | 224.74 | 626.87 |
| 10 | 292.09 | 397.85 | 409/45 | 539.76 | 955.22 |
| 20 | 197.50 | 359.85 | 370.83 | 322.89 | 985.71 |
| 30 | 172.94 | 292.21 | 212.60 | 243.37 | 912.33 |
| 45 | 45.63 | 95.00 | 79.23 | 240.96 | 834.55 |
| 60 | 15.68 | 86.32 | 78.46 | 86.00 | 540.00 |
| 90 | 3.05 | 80.52 | 66.93 | 70.00 | 358.21 |
| 120 | 0.53 | 58.57 | 47.24 | 35.00 | 226.87 |
| 180 | 0.00 | 10.34 | 48.72 | 37.50 | 55.56 |

From the tissue and sera studies it was determined that there is a rapid fall in plasma concentration of physostigmine that is followed by a slow decline during the elimination phase. The estimated plasma half-life during the rapid decline phase is approximately 15 min. Physostigmine has a high degree of lipid solubility and is therefrom rapidly distributed to central as well as peripheral tissues. Within 2.5 min it is present in all of the tissues studied. The highest tissue concentrations of physostigmine were found in the heart and spleen. The levels of the drug found in the brain is consistent with its tertiary amine structure. The high, sustained levels of the drug in the spleen, which continued to increase for 20 min. during the same time the drug levels in plasma and other tissues were decreasing, were not expected but may be due to drug binding to cholinesterase in the tissue.

In order to prove the specificity of the antibody of the present invention, HPLC analysis was conducted. The HPLC system consisted of Waters Associates liquid chromatograph equipped with a 6000 A solvent delivery system, a Model 441 absorbance detector, a U6K injector, a model 720 system controller, an Omni Scribe recorder (Houston Instruments, Houston, Tex.), a model cygnet Fraction collector (ISCO, Lincoln, Nebr.).

High pressure liquid chromatography (HPLC) was performed using a model $C_{18}$ u Bondapak column (30 cm×0.39 cm. lid) (waters). The Uv detector was fixed at 245 nm with range set at 0.005 absorbance units full scale and flow rate of the mobile phase adjusted to 2 ml/min. A 100-ul sample loop was used to load the column. The mobile phase consisted of an aqueous solution of 0.015 m each of monobasic sodium phosphate and sodium salt of beptanesulfonic acid, and methanol (57.5:42.5 V/V).

The column was operated at ambient temperature. After injecting samples into the HPLC column, the effluent was collected every 20 seconds; the solvent was evaporated using a vacuum centrifuge (speed Vac concentrator, Savant Instruments Inc., Hicksville, N.Y.). Each residue was then reconstituted using the assay buffer and was analyzed for physostigmine by the RIA. The antibody only bound to material in the fractions which came off the column at the time that the standard physostigmine was eluted. FIG. 1 consists of a series of high pressure chromatographs which confirm the specificity of the RIA of the present invention. The slight delay between the peak of immuno-reactivity and maximum absorbance is due to the time required to pass from the detector to the collection valve.

The HPLC method is specific for physostigmine and none of the metabolites co-elute with the parent drug. The fact that HPLC studies demonstrated that physostigmine-like substances in plasma and tissue homogenate samples which bound to the antibody co-eluted with standard physostigmine is evidence of the specificity of the antibodies. The presence of a single immunoreactive peak in the chromatographs indicates that the antibodies do not bind to any of the metabolites of physostigmine which may have formed in-vivo or in-vitro in plasma or tissues.

We claim:

1. A process for determining concentrations of physostigmine in a sample of biological fluid which comprises
   a. mixing said sample with an antibody for physostigmine, said antibody being formed in response to a physostigmine-containing antigen,
   b. determining the extent of binding between said antibody and physostigmine in said sample, and
   c. comparing the measured extent of binding between said antibody and physostigmine in said sample with a known quantitative relationship between an extent of binding and a specific concentration of physostigmine.

2. The process of claim 1, wherein said molecule of said physostigmine containing antigen is comprised of twelve physostigmine molecules.

3. The process of claim 1, wherein the ratio of said physostigmine containing antigen and said biological fluid is 1:150.

4. The process of claim 1, wherein said process can detect concentrations as low as 100 pg physostigmine per 0.1 milliliters of biological fluid.

5. The process of claim 1, wherein said process is unaffected by, and will not detect, the presence of the major metabolites of physostigmine.

6. The process of claim 1, wherein said binding reaction is effected by mixing a sample of physostigmine labeled with a radioactive isotope with said antibody to effect binding of physostigmine with said antibody and separating said bound material to said antibody.

7. The process of claim 6, wherein said radioactive isotope is tritium.

8. The process of claim 1, wherein said means is produced by a process which comprises
   a. diazotizing para-aminobenzoic acid by reacting it with hydrochloric acid and sodium nitrite,
   b. reacting said diazotized para-aminobenzoic acid with physostigmine to form a said physostigmine p-aminobenzoic, and
   c. reacting said physostigmine-hapten with bovine serum albumin.

* * * * *

UNITED STATES PATENT AND TRADEMARK OFFICE
CERTIFICATE OF CORRECTION

PATENT NO. : 5,252,495
DATED : 12 October 1993
INVENTOR(S) : Russell L. MILLER, Jr. et al.

It is certified that error appears in the above-indentified patent and that said Letters Patent is hereby corrected as shown below:

| Column | Line | |
|---|---|---|
| 1 | 8 | Change "a" to --an--. |
| 3 | 58 | Change "polyclonal/antibodies" to --polyclonal antibodies--. |
| 3 | 59 | After "determine" insert --the presence of--. |
| 5 | 18 | Before "recovered" insert --is--. |
| 6 | 54 | Change "has" to --had--. |
| 7 | 6 | Change "were" to --being--. |
| 7 | 56 | Change "Of" to --of--. |
| 7 | 68 | Change "convenience" to --convenient--. |
| 8 | 51 | After "inhibition" insert --($IC_{50}$)--. |
| 9 | 56 | Change "Was" to --was--. |
| 9 | 59 | Change "Washed" to --washed--. |

UNITED STATES PATENT AND TRADEMARK OFFICE
CERTIFICATE OF CORRECTION

PATENT NO. : 5,252,495
DATED : 12 October 1993
INVENTOR(S) : Russell L. MILLER, Jr., et al.

It is certified that error appears in the above-indentified patent and that said Letters Patent is hereby corrected as shown below:

| Column | Line | |
|---|---|---|
| 9 | 60 | Change "1 um" to --1 μm--. |
| 11 | 19 | After "antigen," insert --said physostigmine containing antigen being formed by synthesizing a physostigmine p-aminobenzoic acid hapten and reacting said hapten with an immunogenic carrier material,--. |
| 12 | 18 | Change "means" to --antigen--. |
| 12 | 24 | After "p-aminobenzoic" insert --acid hapten--. |

Signed and Sealed this

Twenty-first Day of June, 1994

Attest:

Bruce Lehman

BRUCE LEHMAN

*Attesting Officer* *Commissioner of Patents and Trademarks*